US011250952B1

(12) United States Patent
Kirnak

(10) Patent No.: US 11,250,952 B1
(45) Date of Patent: Feb. 15, 2022

(54) METHOD OF EVENT-DRIVEN HEALTH AND WELLNESS DECISION SUPPORT

(71) Applicant: Alean Kirnak, Encinitas, CA (US)

(72) Inventor: Alean Kirnak, Encinitas, CA (US)

(73) Assignee: Software Partners LLC, Encinitas, CA (US)

(*) Notice: Subject to any disclaimer, the term of this patent is extended or adjusted under 35 U.S.C. 154(b) by 0 days.

(21) Appl. No.: 16/104,105

(22) Filed: Aug. 16, 2018

Related U.S. Application Data

(60) Provisional application No. 62/546,515, filed on Aug. 16, 2017.

(51) Int. Cl.
  *G16H 50/20* (2018.01)
  *G16H 10/60* (2018.01)
  *G06F 16/22* (2019.01)

(52) U.S. Cl.
  CPC ......... *G16H 50/20* (2018.01); *G06F 16/2291* (2019.01); *G16H 10/60* (2018.01)

(58) Field of Classification Search
  CPC ........ G16H 10/60; G16H 15/00; G16H 40/63; G16H 40/20; G16H 50/30; G16H 50/20; G16H 40/67; G16H 50/50; G16H 10/40; G16H 20/00; G16H 50/70; G16H 70/20; G16H 80/00; G16H 50/80; G06Q 50/24; G06Q 50/22; G06Q 10/10; G06F 19/3418; G06F 19/3456; G06F 19/00; G06F 19/3481; G06F 19/325; G06F 19/3468; G06F 19/3475
  See application file for complete search history.

(56) References Cited

U.S. PATENT DOCUMENTS

| 2006/0272652 A1* | 12/2006 | Stocker | G16H 50/50 128/898 |
|---|---|---|---|
| 2008/0147443 A1* | 6/2008 | Scherpbier | G06Q 50/22 705/3 |
| 2010/0131293 A1* | 5/2010 | Linthicum | G16H 10/60 705/3 |
| 2011/0131055 A1* | 6/2011 | Grady | G06Q 10/06 705/2 |
| 2011/0145012 A1* | 6/2011 | Nightingale | G06F 19/3481 705/3 |
| 2012/0150878 A1* | 6/2012 | Naeymi-Rad | G06F 16/22 707/752 |
| 2017/0262604 A1* | 9/2017 | Francois | G16H 70/60 |

* cited by examiner

*Primary Examiner* — Joseph D Burgess

(57) ABSTRACT

The method of event-driven health and wellness decision support considers an individual's medical records and lifestyle; applies healthcare best practices; and recommends next steps.

Medical and lifestyle records are input, converted to events and inserted in timestamp order in an event queue. Events are processed in queued order by handlers, and results recorded in a data structure called a "person state". Some handlers create additional events and insert them in the event queue in timestamp order. Those events are in turn processed in timestamp order. Other handlers create no events, allowing processing of all queued events to eventually complete. After events representing actual occurrences are processed, events representing postulated activities are created, queued, and processed until a specific patient state representing a health and wellness goal obtains. This allows several activity paths to be compared to determine the best path to an optimal health goal. Next steps are recommended as output.

9 Claims, 7 Drawing Sheets

| | | | | | | | | | |
|---|---|---|---|---|---|---|---|---|---|
| Series | Diphtheria standard series | | | | | | | | |
| Target Disease | Diphtheria | | | | | | | | |
| Select Patient Series | Default Series | Product Path | Series Group | Series Group ID | Series Priority | Series Pref | Min Age To Start | Max Age To Start | |
| Select Patient Series | Yes | No | Standard | 1 | A | 1 | n/a | n/a | |
| Dose | Dose 1 | | | | | | | | |
| Age | Absolute Min Age | Min Age | Earliest Rec Age | Latest Rec Age (<) | Max Age (<) | | | | |
| Age | 6 wks - 4 days | 6 wks | 2 mos | 3 mos + 4 wks | n/a | | | | |
| Cond Skip | Set Logic | Set ID | Description | Begin Age | Dose Count Logic | | | | |
| Cond Skip | OR | 1 | Not required for those 7 yrs or older | 7 yrs | n/a | | | | |
| Cond Skip | OR | 2 | Not required if patient has received 6 or more total doses to date | 6 wks - 4 days | greater than | | | | |
| Dose | Dose 2 | | | | | | | | |
| Age | Absolute Min Age | Min Age | Earliest Rec Age | Latest Rec Age (<) | Max Age (<) | | | | |
| Age | 10 wks - 4 days | 10 wks | 4 mos | 5 mos + 4 wks | n/a | | | | |
| Pref Interval | From Immediate Previous Dose Administered? | From Target Dose | From Most Recent (CVX List) | From Relevant Observation (Code) | Absolute Min Interval | Min Interval | Earliest Rec Interval | Latest Rec Interval (<) | |
| Pref Interval | Y | n/a | n/a | n/a | 4 wks - 4 days | 4 wks | 8 wks | 13 wks | |

Fig. 3

| Antigen | Series Name | Dose# | Min Valid Age | Min Valid Interval | Recommended Age | Recommended Interval |
|---|---|---|---|---|---|---|
| Diphtheria | Standard | | | | | |
| | | 1 | 6w-4d | NA | 2m | NA |
| | | 2 | 10w-4d | 4w-4d | 4m | 4w |
| | | 3 | 14w-4d | 4w-4d | 6m | 4w |
| | | 4 | 12m-4d | 6m-4d | 15m | 6m |
| | | 5 | 4y-4d | 6m-4d | 4y | 6m |
| | | 6 | 7y | 4w-4d | 7y | 4w |
| | | 7 | 7y | 6m-4d | 7y | 6m |
| | | 8 | 7y | 6m-4d | 7y | 6m |
| | | 9 | 7y | NA | 11y | NA |
| | | 10 | NA | 2y | NA | 5y |

Fig. 4

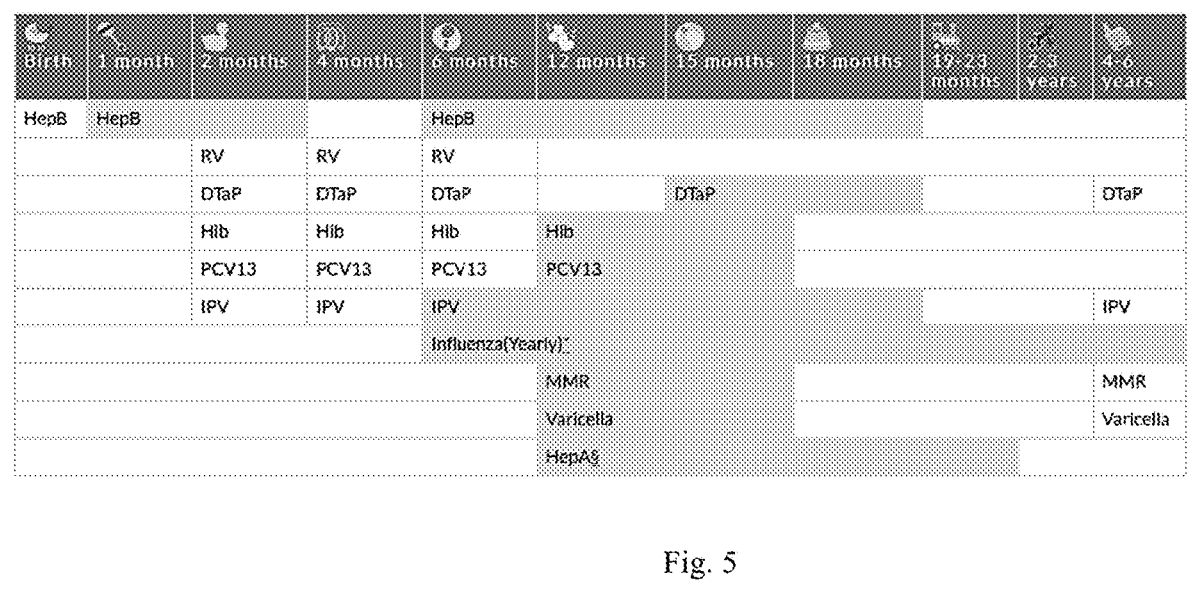

| Birth | 1 month | 2 months | 4 months | 6 months | 12 months | 15 months | 18 months | 19-23 months | 2-3 years | 4-6 years |
|---|---|---|---|---|---|---|---|---|---|---|
| HepB | HepB | | | HepB | | | | | | |
| | | RV | RV | RV | | | | | | |
| | | DTaP | DTaP | DTaP | | DTaP | | | | DTaP |
| | | Hib | Hib | Hib | Hib | | | | | |
| | | PCV13 | PCV13 | PCV13 | PCV13 | | | | | |
| | | IPV | IPV | IPV | | | | | | IPV |
| | | | | Influenza(Yearly) | | | | | | |
| | | | | | MMR | | | | | MMR |
| | | | | | Varicella | | | | | Varicella |
| | | | | | HepA§ | | | | | |

Fig. 5

| late | past due | recommended | min recommended | eligible | due in future |

| Group | Dose | Eligible Date | Min Rec Date | Rec Date | Past Due Date |
|---|---|---|---|---|---|
| DTaP/Tdap/Td | 1 | 06/16/1996 | 06/20/1996 | 07/09/1996 | 09/05/1996 |
| HepA | 1 | 05/05/1997 | 05/09/1997 | 05/09/1997 | 06/05/1998 |
| HepB | 1 | 05/09/1996 | 05/09/1996 | 05/09/1996 | 06/05/1996 |
| Hib | 1 | 06/16/1996 | 06/20/1996 | 07/09/1996 | 09/05/1996 |
| HPV | 1 | 05/05/2005 | 05/09/2005 | 05/09/2007 | 06/05/2009 |
| Influenza | 1 | 11/05/1996 | 07/01/2017 | 07/01/2017 | |
| Meningococcal | 1 | 05/09/2006 | 05/09/2007 | 05/09/2007 | 06/05/2009 |
| MMR | 1 | 05/05/1997 | 05/09/1997 | 05/09/1997 | 10/06/1997 |
| Pneumococcal | 1 | 06/16/1996 | 06/20/1996 | 07/09/1996 | 09/05/1996 |
| Polio | 1 | 06/16/1996 | 06/20/1996 | 07/09/1996 | 09/05/1996 |
| Rotavirus | 1 | 06/16/1996 | 06/20/1996 | 07/09/1996 | |
| Varicella | 1 | 05/05/1997 | 05/09/1997 | 05/09/1997 | 10/06/1997 |
| Zoster | 1 | 05/09/2014 | 05/09/2046 | 05/09/2046 | |

Fig. 6

| late | past due | recommended | min recommended | eligible | due in future |

| Group | Dose | Eligible Date | Min Rec Date | Rec Date | Past Due Date |
|---|---|---|---|---|---|
| DTaP/Tdap/Td | 1 | 06/16/1996 | 06/20/1996 | 07/09/1996 | 09/05/1996 |
| HepA | 1 | 05/05/1997 | 05/09/1997 | 05/09/1997 | 06/05/1998 |
| HepB | 1 | 05/09/1996 | 05/09/1996 | 05/09/1996 | 06/05/1996 |
| Hib | 1 | 06/16/1996 | 06/20/1996 | 07/09/1996 | 09/05/1996 |
| HPV | 1 | 05/05/2005 | 05/09/2005 | 05/09/2007 | 06/05/2009 |
| Influenza | 1 | 11/05/1996 | 07/01/2017 | 07/01/2017 | |
| Meningococcal | 1 | 05/09/2006 | 05/09/2007 | 05/09/2007 | 06/05/2009 |
| MMR | 1 | 05/05/1997 | 05/09/1997 | 05/09/1997 | 10/06/1997 |
| Pneumococcal | 1 | 06/16/1996 | 06/20/1996 | 07/09/1996 | 09/05/1996 |
| Polio | 1 | 06/16/1996 | 06/20/1996 | 07/09/1996 | 09/05/1996 |
| Rotavirus | 1 | 06/16/1996 | 06/20/1996 | 07/09/1996 | |
| Varicella | 1 | 05/05/1997 | 05/09/1997 | 05/09/1997 | 10/06/1997 |
| Zoster | 1 | 05/09/2014 | 05/09/2046 | 05/09/2046 | |

Fig. 7

METHOD OF EVENT-DRIVEN HEALTH AND WELLNESS DECISION SUPPORT

CROSS-REFERENCE TO RELATED APPLICATION

This application claims the benefit of U.S. Provisional Patent Application Ser. No. 62/546,515, filed on Aug. 16, 2017.

BACKGROUND

1. Field

The disclosure of the present patent application relates to health and wellness, and particularly to a method of driving healthcare and lifestyle actions toward optimal quantifiable results.

2. Description of the Related Art

The healthcare field makes use of applications generally referred to as "clinical decision support". Similarly, in the wellness or lifestyle field, such applications are often referred to as "wellness apps". These software applications support decisions at points in time based upon a body of best practices to drive toward optimal individual health. Clinical decision support tends to support the healthcare professional providing care to an individual, while wellness apps tend to support the individual himself.

Two challenges come into play: first, to understand the individual's condition as a result of natural, healthcare and activity events occurring over time; and second, to consider best practices to determine the recommended next set of actions to take at the present and in the future. Thus, a method of event-driven health and wellness decision support is needed for solving the aforementioned problems is desired.

SUMMARY

The method of event-driven health and wellness decision support quickly computes an individual's present health and wellness state from his medical records such as electronic or paper medical records, and from his lifestyle records such as food and activity tracking; applies healthcare best practices; and recommends next steps to be taken at present or on to future dates. It should be understood that the calculations may be performed by any suitable computer system. Medical and lifestyle records are entered via any suitable type of user interface or electronic interface, and read into any suitable type of computer readable and programmable memory. It may be stored in a non-transitory, computer readable storage medium. Calculations are performed by any suitable type of computer processor. Results may be returned electronically to another computer system, or displayed to the user on any suitable type of computer display.

Upon receiving medical and lifestyle records, the method creates events associated with the individual according to the types of natural event, or healthcare or lifestyle activity that each record represents, transfers the timestamps of those activities to the created events. It queues the events in timestamp order in an event queue. The method then processes the events in their queued order by executing a specific handler associated with each event type. Upon completing execution, each handler records the accumulated effects of the event just processed by updating a complex data structure associated with the individual called a "person state". As they execute, some handlers create additional events and insert them in the event queue in timestamp order. Those events are in turn processed by the method of event-driven health and wellness decision support as they are encountered. Other handlers create no events, allowing processing to eventually reach the end of the event queue.

The input records may reflect actual occurrences in the real world. In another embodiment, the input records may reflect fictitious occurrences, allowing the method of event-driven health and wellness decision support to be used for simulation purposes. In the preferred embodiment, the input records reflect actual occurrences, then at the point at which event queue processing reaches the current date and time, the method creates events representing postulated future health and wellness activities, inserts them into the event queue, then continues processing until a specific patient state representing a health and wellness goal obtains. This allows the invention to be used to compare several activity paths, determine which is most effective in reaching an optimal health goal, and recommend the steps that lead to that state as output.

These and other features of the present method of event-driven health and wellness decision support will become readily apparent upon further review of the following specification.

BRIEF DESCRIPTION OF THE DRAWINGS

FIG. 3 is a table of supporting data for example immunization best practices.

FIG. 4 is a table of example immunization best practices translated into a format suitable for input to the method of event-driven health and wellness decision support.

FIG. 5 illustrates an example vaccination schedule for an idea patient with no special conditions.

FIG. 6 illustrates an example vaccine recommendation after a birth event on 5/9/1996 has been processed.

FIG. 7 illustrates an example vaccine recommendation after a vaccine eligibility event on 6/16/1996 has been processed.

DETAILED DESCRIPTION OF THE PREFERRED EMBODIMENTS

Figure 1:
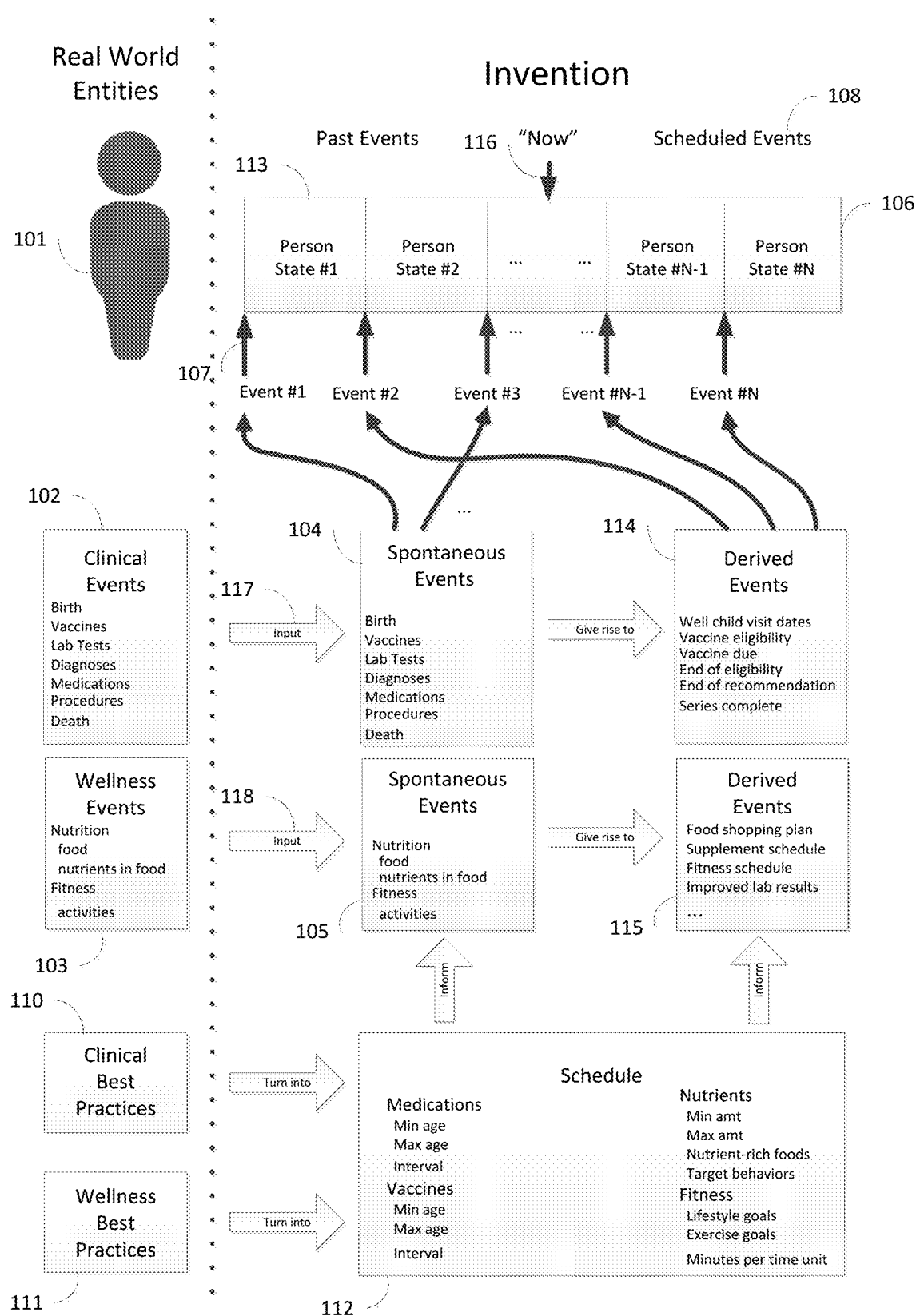
FIG. 1 is a block diagram illustrating the core modules and steps in the method of event-driven health and wellness decision support.

In the following, it should be understood that the term "person" refers to an individual person; for example, Tatiana Wright.

The term "health-and-wellness record" refers to a computer-readable representation of a real world event or events related to a person's health and wellness, including an explicit, implicit or presumed timestamp. Examples include: birth records, vaccine records, blood test results, food journals.

The term "record type" refers to a value associated with a health-and-wellness record that indicates the kind of real world event it represents. Examples include "birth record (1)", "vaccine record (2)", "lipid panel (3)", "daily food journal (4)".

The term "Now" refers to a computer representation of a point in time to some degree of accuracy, such as to the nearest month, day, hour or minute, for example, 5/9/1996. "Now" represents virtual, rather than real world, present time.

The term "event" refers to a computer representation of something that happens in the real world; for example, Tatiana Wright is born.

The term "event type" refers to a value associated with an event that indicates the kind of real world event it represents; for example, "birth event (1)".

The term "spontaneous event" refers to an event that is created by the method of event-driven health and wellness decision support upon receiving a health-and-wellness record; for example, a birth event.

The term "handler" refers to a software module that is executed to process events of a particular type; for example, a birth event handler.

The term "derived event" refers to an event that is created, updated or deleted by the handler of another event; for example, a vaccine recommendation event.

The term "schedule" refers to a set of data elements serving as parameters to handlers that describe clinical best practices; for example, Centers for Disease Control's (CDC's) Clinical Decision Support for Immunization (CDSi) Supporting Data.

The term "person state" refers to a composite set of data elements representing a person's health and wellness state; for example, Tatiana Wright is three years old and is due for a vaccine.

FIG. 1 depicts real world entities, such as individual persons 101, clinical and wellness events 102 and 103, clinical and wellness best practices 110 and 111, as distinct from their software representations by the method of event-driven health and wellness decision support.

Representations of real world events are created in the form of electronic records by means external to the method of event-driven health and wellness decision support, for example, by Electronic Health Record (EHR) systems, by apps executing on mobile devices or tablets, or by users via data entry screens. These electronic "health-and-wellness" records are then received as input to the method of event-driven health and wellness decision support.

Each health-and-wellness record contains certain information, including:
1. The type of real world event it represents ("event type");
2. The individual person it happened to; and
3. A timestamp.

For example, in one instance, the health-and-wellness record may comprise a birth record that provides a unique person identifier, the person's name, gender and date of birth.

In general, health-and-wellness records 117 and 118 may be formatted in any of a variety of ways, such as Health Level Seven (HL7) messages, web service payloads, or as transmissions from a data entry screen, user app or web application. In one embodiment, the health-and-wellness records may be received in a batch; in another embodiment, serially over time.

Note that nothing in the method of event-driven health and wellness decision support prevents a health-and-wellness record from representing more than one real world event, individual person, or timestamps. Such composite health-and-wellness records are the equivalent of multiple simple health-and-wellness records and are treated as such by the method of event-driven health and wellness decision support.

A birth record for a female person named Tatiana Wright born on 5/9/1996 is an example of a health-and-wellness record 117.

Upon receiving each health-and-wellness record, the method of event-driven health and wellness decision support creates a computer representation of it ("event"). Each event 104 and 105 is associated with the individual person 101 ("person") that is the subject of the real world event. Each event has a timestamp based upon the when the real world event occurred; for example, 5/9/1996. The timestamp may also indicate a range; for example, Tatiana Wright may have been ill from 6/15/1996 until 6/20/1996. Each event is assigned an "event type" equal to one in a finite, discrete set of event types describing the type of real world event the health-and-wellness record represents. Each event type is associated with a handler, which is a software method (subroutine, procedure) used to process the event. Each event is inserted into an event queue 107.

For example, upon receiving the former birth record for Tatiana Wright, the method of event-driven health and wellness decision support creates a "birth" event associated with Tatiana Wright and having a timestamp of 5/9/1996. The newly created birth event is associated with the birth event handler and inserted into the event queue.

Handlers maintain instances of a complex data structure ("person state" 106) associated with an individual person (such as Tatiana Wright). Each person state is timestamped with beginning and ending effective dates to indicate the range for which it is effective. The data elements of the person state describe the health-and-wellness state of an individual person over the effective range. For example, an immunization embodiment whose purpose is to drive toward immunity to a set of antigens may maintain the tested or presumed immunity status of each target antigen in the person state. As the data elements in the person state are created, updated and deleted by handlers, multiple instances of a person state may obtain for a common individual person, with different, contiguous effective date ranges.

The specific set of data elements required in the person state are informed by the "schedule" 112 which may be input to the method of event-driven health and wellness decision support at startup or at a later point in time. The schedule comprises a set of data elements used to model clinical best practices 110 and 111. Each schedule is associated with a range of effective dates reflective of the period in which the clinical practices it models are in effect. The specific data elements that comprise the person state, and the set of values which each data element may take on, vary with the domain of the embodiment. For example, the data elements used for an immunization domain may differ from those used in a nutrition domain. A single embodiment of the method of event-driven health and wellness decision support may generate either or both sets of data elements.

An example of real world clinical best practices is indicated by the section of Centers for Disease Control (CDC) vaccine schedules given in FIG. 3. An example vaccine schedule section in a format that the method of event-driven health and wellness decision support can conveniently convert to a schedule 112 is given in FIG. 4. The example CDC vaccine schedule specifies:
1. A set of disease-causing antigens for which vaccines are recommended;
2. For each antigen, a set of series of vaccine doses which may be administered to achieve presumed immunity to the antigen;
3. For each series, a set of doses of vaccine;

4. For each dose:
   a. ages at which an administered dose is be considered valid if given;
   b. ages at which an administered dose is recommended;
   c. required and recommended intervals between doses;
   d. lists of specific vaccine products that are preferred, allowed, tolerated and considered extras or boosters;
   e. other demographics such as patient gender, occupation, etc. which may affect dose administration; and
   f. other details and instructions.

Best practices such as the CDC schedule of FIG. 3 are input in an appropriate format such as that of FIG. 4 and converted by the method of event-driven health and wellness decision support into schedules 112. Handlers then use the data elements of the schedule in effect Now—that is, at the point in time matching the timestamp of the event the handler is processing—to update data elements in the person state and to create, update and delete derived events.

Handlers may delete and/or create other events as appropriate to the type of event the handler is processing. To distinguish between events representing real world events and events generated by the method of event-driven health and wellness decision support, events created in response to receiving a health-and-wellness record are called "spontaneous events" 104 and 105 while events created by handlers of other events are called "derived events" 114 and 115.

The method of event-driven health and wellness decision support processes the events in the event queue in order. Each event in the queue is processed by executing its handler. Conceptually, each handler pretends that real world time is actually the date and time indicated on the event timestamp by setting Now 116 to the event timestamp. For example, the birth event handler for Tatiana Wright, knowing Tatiana Wright's date of birth and gender as well as the clinical best practices then in use, might schedule due dates for Tatiana Wright's infant vaccines as they would have been scheduled at the time of her birth. The handler only makes use of what could have been known on her real world date of birth. It has no access to information that could not have been known at that time, for example, an illness she might have contracted weeks, months or years after her birth, even if such events are known at the time the method of event-driven health and wellness decision support executes.

The method of event-driven health and wellness decision support represents the date of the event being processed in a data element called Now 116. For example, when processing Tatiana Wright's birth record, "Now" is set to 5/9/1996. Events in the event queue whose timestamps are earlier than Now are "past events" 113. Events in the event queue 106 whose timestamps are later than Now are "scheduled events" 108.

Continuing with the Tatiana Wright example, the birth event handler may create "vaccine eligibility" events with timestamps representing the dates at which the real world Tatiana Wright could receive vaccines that would be considered clinically "valid" according to clinical best practices that require infants to reach a certain age before receiving certain vaccines. The birth handler computes the timestamps of the vaccine eligibility using the value of Now of 5/9/1996 (Tatiana's date of birth) and upon the immunization schedule that was in effect at Now. FIG. 6 illustrates the dates at which various vaccines become eligible and due after processing Tatiana's birth event with Now set to 5/9/1996, as recorded in her patient state. Tatiana's birth event handler creates a vaccine eligibility event with the timestamp set to 6/16/1996 and inserts it into the event queue. When the vaccine eligibility handler executes, it sets Now to 6/16/1996, and updates the person state to indicate that as of Now (6/16/1996), Tatiana is eligible to receive a particular vaccine. FIG. 7 illustrates that after processing the eligibility handler on 6/16/1996, vaccines have now become eligible, as illustrated by the light shading. An "administered vaccine" event handler with an event date after 6/16/1996 may consult this person state to determine that a vaccine dose that Tatiana received was "valid".

In a similar manner, the birth event handler may create "vaccine due" events with timestamps representing the dates at which the real world Tatiana Wright would be recommended for vaccines. When the vaccine due handler executes, it updates the person state to indicate that Tatiana is due for a particular vaccine. It may also trigger a reminder to Tatiana or her healthcare provider. Alternatively, Tatiana or her healthcare provider may query her person state to discover what vaccines she is due for.

If the administered vaccine handler determines an administered vaccine was "valid", it might compute the necessary waiting period based upon the schedule, then create an event representing when the next vaccine dose is due. Alternatively, it may determine from the schedule that Tatiana has received enough doses of this vaccine, wherein it would update her person state to indicate she is presumed immune to the target antigen. In the latter case, no more vaccines are needed, so no future vaccine dose events need be created.

If an administered dose is determined to be "invalid", Tatiana may be required to receive the vaccine dose again after waiting some period of time. In this case, the handler might update Tatiana's person state to indicate that as of Now she is ineligible to receive a dose, delete any queued "vaccine eligibility" event in consideration of the new waiting period, then repeat the process of scheduling future vaccine eligibility and vaccine due events with the appropriate future timestamps, and insert them into the event queue.

This process will continue until presumed immunity is achieved.

As illustrated in FIG. 6 and FIG. 7, vaccines are available against dozens of antigens. The method of event-driven health and wellness decision support may create and process events for many vaccine series in parallel. Output may be delivered to users in response to queries from a user interface or remote computer system; alternatively, reminders may be "pushed" to the user. In this manner, the method of event-driven health and wellness decision support will drive care optimally toward immunity to each of multiple vaccine-preventable diseases.

Event handlers compute interactions among events in the event queue by creating, updating and deleting events accordingly. For example, clinical best practices dictate that certain intervals be respected, not only between doses of vaccines against the same antigen, but between doses of classes of vaccines, such as live virus vaccines.

Note that in one embodiment, the method of event-driven health and wellness decision support is capable of pausing event processing, then resuming. For example, when Now reaches the present date, the method of event-driven health and wellness decision support may pause until the present date "catches up" with the next event in the queue.

In another embodiment, the method of event-driven health and wellness decision support continues processing of scheduled events, advancing Now past the present real world date, until particular targeted events are encountered and processed. For example, the method of event-driven health and wellness decision support may continue processing events in the event queue until future vaccine due dates are encountered, in order to respond to a query for next due dates. Note that this is distinct from merely reporting the dates at which vaccine due events are queued, as processing intervening events can results in those queued events to be deleted and rescheduled. The method of event-driven health and wellness decision support is the more accurate approach, especially in embodiments where schedules are complex and there are many interactions among events.

The method of event-driven health and wellness decision support may also continue processing until a specified health and wellness goal is reached, for the purpose of determining the best future path to the goal. This is especially useful when alternate paths are possible and the optimal one is not obvious to the user. To accomplish this, the method of event-driven health and wellness decision support processes events in the event queue up to the point in time when a next-step decision must be made; for example, up to Now equal to the present time. At that point, events are created representing postulated alternate paths, queued, and processed, until a desired goal, as represented by a specified patient state, is reached by one or more of them. Essentially, possible future paths are simulated, and the results compared. The results may then be returned to the user.

Returning to the immunization example, upon being queried for a next dose recommendation against an antigen for which numerous alternate vaccine series exist, the method of event-driven health and wellness postulates that each dose of each alternate series is given at the optimal time until presumed immunity is reached. It creates events representing all these doses, inserts them into a copy of the event queue, and processes each queue until the target antigen status reaches "presumed immune" or until another antigen status indicating the desired "presumed immune" state cannot be reached obtains; for example, if "aged out" status is attained. It could be discovered, for example, that the individual ages out of one series prior to completion, but can attain immunity via another series. This results may be returned to the user, who may thereby decide to pursue the immunity-producing alternative.

In another embodiment, all the events may be postulated. Input events may not represent actual events that occurred in the real world, but rather scenarios for purposes of simulation. The method of event-driven health and wellness decision support continues to process all scheduled events, advancing Now past the present real world date, until the end of the queue is reached.

In one embodiment, health-and-wellness records may be received in timestamp order.

In another embodiment, input events may be received out of timestamp order. The method of event-driven health and wellness decision support is also capable of "backtracking"—of re-setting Now to an earlier date, and re-processing the event queue from that point forward. This may involve saving the event queues and the person states as events are processed so as to be able to return to any point in the event queue and re-process events.

Figure 2:
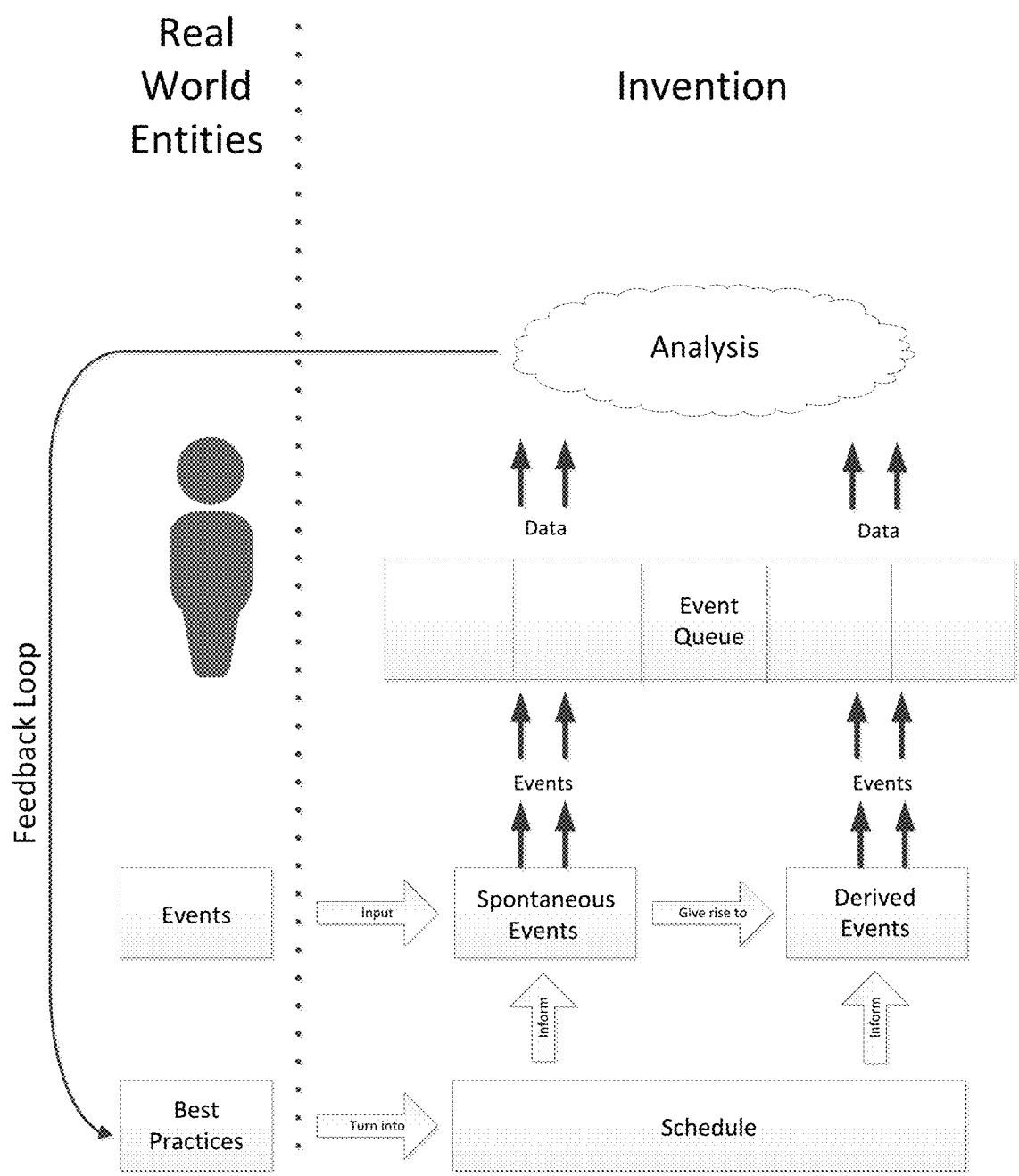
FIG. 2 is a block diagram illustrating the analysis and feedback aspects of the method.

In another embodiment, the method of event-driven health and wellness decision support may compute and save all the person states for analysis purposes as in FIG. 2. For example, the set of person states for a population of individuals may be analyzed may to determine how close to their due dates vaccines were administered; or alternatively, how often an opportunity (based upon a visit to a provider) to give a vaccine might have been missed.

In another embodiment, the method of event-driven health and wellness decision support may create several events queues and insert events associated with a common individual person into various of these for sequential processing. In other words, event processing for events associated with a common individual person can be multi-threaded. This can occur when there are no dependencies among the sets of event types inserted into different queues; in other words, when processing is "thread-safe".

In one embodiment, multiple instances of person states do not need to be retained. In this embodiment, the method of event-driven health and wellness decision support continually updates a single instance of a person state, processing each event in the event queue until Now reaches a target timestamp. This is useful in embodiments that implement a "stateless service". For example, wherein the objective is to query for the status of past vaccines and future vaccine due dates as of a particular point of time (commonly, today), supplying the necessary person demographics and all the health-and-wellness records as input to the service call.

It is to be understood that the method of managing personal health care records and schedules is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

It is to be understood that while the preferred embodiment applies the method of event-driven health and wellness decision support to one individual, the method may easily be replicated to apply to a population.

The task of clinical decision support conceptually is to assess the person state and determine what the next action should be. In other words, it's a state-driven model, where the universe of possible states is described, and some criteria, such as a "rule", determines the transition to a next state.

The challenge here is in the number of possible states and the number of transitions to next states that must therefore be described. The field of mathematics known as "combinatorics" governs the number of possible states. In the context of the method of the method of event-driven health and wellness decision support, the number of person states grows exponentially with the size of the schedule and the number of events.

Consider for example the number of different values that person state may take on with regard to the immunization example. Based upon standard CDC schedules, the composite set of data elements of the person state may take on any combination of the following distinct values:

TABLE 1

Example Person State Data Elements and Number of Distinct Values

| Factor | Average # of Distinct Values |
|---|---|
| Demographic factors: Gender, age, occupation, environment contraindications, etc. | 100 |
| Target antigens | 20 |
| Series per antigen | 4 |
| Doses per vaccine | 3 |
| Preferred products per dose | 6 |
| Due dates and other factors as specified in FIG. 3 | 10 |

As illustrated in FIG. 3, the schedule specifies numerous parameters for each dose of each vaccine series such as to earliest and latest ages that it can be given, as well as a set of products that is appropriate to administer. Based upon the possible combinations of the factors alone, it can be estimated that at least 1,440,000 person states are possible. This number grows when the possible immunization histories of individuals are considered. U.S. vaccine schedules currently recommend on the order of forty vaccines for school-aged children alone. The number of codes in codesets used to record administered vaccines numbers in the hundreds each. Combine this with the fact that an individual person may live a hundred years, the number of possible vaccine histories is too large to practically be enumerated. It is easily possible for that number to grow even more. Consider for example travel vaccine schedules where each country potentially visited has different vaccine requirements. A schedule covering 100 possible countries to be visited has the potential to increase the size of the schedule by several orders of magnitude more.

Without such a method as event-driven health and wellness decision support, it becomes impractical to anticipate all person states and create rules governing the recommended actions and transitions to all other reasonable states. What often happens is that rules are only created for the more common person states. For example, consider the CDC recommended vaccine schedules of FIG. 5. The schedules of FIG. 5 represent the vaccines of an ideal patient with no special conditions who receives each vaccine on exactly the recommended date. FIG. 5 essentially reflects a simulation.

To further understand the complexity of vaccine schedules, the table below illustrates the patient state in the vaccine example of Tatiana Wright at the age of one year and after three vaccines.

TABLE 2

Example patient state

| antigen | antigen status | series | dose | dose status | forecast date | preferred CVX |
|---|---|---|---|---|---|---|
| Cholera | Not Immune | | | | | |
| | | Cholera 1-dose series | | | | |
| Diphtheria | Not Immune | | | | | |
| | | Diphtheria standard series | 4 | Eligible | May 5, 1997 | 20, 28, 106, 120 |
| | | | 1 | Valid | Jul. 9, 1996 | 120 |
| | | | 2 | Valid | Sep. 9, 1996 | 120 |
| | | | 3 | Valid | Nov. 9, 1996 | 120 |
| Hep A | Not Immune | | | | | |
| | | HepA 2-dose series | 1 | Recommend | May 9, 1997 | 52, 83 |
| | | HepA risk 2-dose series | | | | |
| | | HepA risk Twinrix 3 dose series | | | | |
| | | HepA risk Twinrix 4 dose Series | | | | |
| HepB | Not Immune | | | | | |
| | | HepB 3-dose series | 1 | Past Due | Jun. 5, 1996 | 8, 43, 44, 110, 189 |
| | | HepB 4-dose series | 1 | Past Due | Jun. 5, 1996 | 8, 110, 189 |
| | | HepB adolescent 2-dose series | 1 | Due in Future | May 9, 2007 | 43 |
| | | HepB-CpG 2-dose series | 1 | Due in Future | May 9, 2014 | 189 |
| | | HepB risk 3-dose series | | | | |
| | | HepB-CpG risk 2-dose series | | | | |
| | | HepB risk Twinrix 3 Dose Series | | | | |
| | | HepB risk Twinrix 4-dose series | | | | |
| | | HepB risk Recombivax 3-dose series | | | | |
| | | HepB risk Engerix-B 4-dose series | | | | |
| Hib | Not Immune | | | | | |
| | | Hib start at 2 months 4-dose series | 4 | Recommend | May 9, 1997 | 48,49, 120 |
| | | | 1 | Valid | Jul. 9, 1996 | 120 |
| | | | 2 | Valid | Sep. 9, 1996 | 120 |
| | | | 3 | Valid | Nov. 9, 1996 | 120 |
| | | Hib start at 7 months 3-dose series | | | | |
| | | | 1 | Invalid | Jul. 9, 1996 | 120 |
| | | | 1 | Invalid | Sep. 9, 1996 | 120 |
| | | | 1 | Invalid | Nov. 9, 1996 | 120 |
| | | Hib start at 12 months 2-dose series | 1 | Recommend | May 9, 1997 | 48,49, 120 |
| | | | 1 | Invalid | Jul. 9, 1996 | 120 |
| | | | 1 | Invalid | Sep. 9, 1996 | 120 |
| | | | 1 | Invalid | Nov. 9, 1996 | 120 |
| | | Hib start at 15 months 1-dose series | 1 | Due in Future | Aug. 9, 1997 | 48,49, 120 |
| | | | 1 | Invalid | Jul. 9, 1996 | 120 |
| | | | 1 | Invalid | Sep. 9, 1996 | 120 |
| | | | 1 | Invalid | Nov. 9, 1996 | 120 |
| | | Hib PRP-OMP 3-dose series | 1 | Past Due | Sep. 5, 1996 | 49 |
| | | Hib risk child 2-dose series | | | | |
| | | | 1 | Extraneous | Jul. 9, 1996 | 120 |
| | | | 1 | Extraneous | Sep. 9, 1996 | 120 |
| | | | 1 | Extraneous | Nov. 9, 1996 | 120 |
| | | Hib risk 1-dose series | | | | |
| | | | 1 | Extraneous | Jul. 9, 1996 | 120 |
| | | | 1 | Extraneous | Sep. 9, 1996 | 120 |
| | | | 1 | Extraneous | Nov. 9, 1996 | 120 |
| | | Hib risk 3-dose series | | | | |
| HPV | Not Immune | | | | | |
| | | HPV female 2-dose series | 1 | Due in Future | May 9, 2005 | 165 |
| | | HPV female 3-dose series | 1 | Due in Future | May 9, 2011 | 165 |
| | | HPV male 2-dose series | | | | |

TABLE 2-continued

Example patient state

| antigen | antigen status | series | dose | dose status | forecast date | preferred CVX |
|---|---|---|---|---|---|---|
| | | HPV male 3-dose series | | | | |
| | | HPV risk male 2-dose series | | | | |
| | | HPV risk female 2-dose series | | | | |
| | | HPV risk female 3-dose series | | | | |
| Influenza | Not Immune | HPV risk male 3-dose series | | | | |
| | | Influenza standard series | 1 | Eligible | Nov. 5, 1996 | 140, 141, 150, 158, 161, 171, 186 |
| Japanese Encephalitis | Not Immune | | | | | |
| | | Japanese Encephalitis risk 2-dose series | | | | |
| Measles | Not Immune | | | | | |
| | | Measles 2-dose series | 1 | Recommend | May 9, 1997 | 3, 94 |
| | | Measles risk 1-dose series | | | | |
| | | Measles risk 2-dose series | | | | |
| Meningococcal | Not Immune | | | | | |
| | | Meningococcal ACWY 2-dose series | 1 | Due in Future | May 9, 2007 | 114,136 |
| | | Meningococcal ACWY risk start before 7 months 4-dose series | | | | |
| | | Meningococcal ACWY risk start after 7 months 2-dose series | | | | |
| | | Meningococcal ACWY risk Hib-MenCY-TT 4-dose series | | | | |
| | | Meningococcal ACWY risk 2-dose series | | | | |
| | | Meningococcal ACWY risk 1-dose series | | | | |
| Meningococcal B | Not Immune | | | | | |
| | | Meningococcal B risk 2-dose series MenB-4C | | | | |
| | | Meningococcal B risk 2-dose series MenB-FHbp | | | | |
| | | Meningococcal B risk 3-dose series MenB-FHbp | | | | |
| Mumps | Not Immune | | | | | |
| | | Mumps 2-dose series | 1 | Recommend | May 9, 1997 | 3, 94 |
| | | Mumps risk 1-dose series | | | | |
| | | Mumps risk 2-dose series | | | | |
| Pertussis | Not Immune | | | | | |
| | | Pertussis standard series | 4 | Eligible | May 5, 1997 | 20, 106, 120 |
| | | | 1 | Valid | Jul. 9, 1996 | 120 |
| | | | 2 | Valid | Sep. 9, 1996 | 120 |
| | | | 3 | Valid | Nov. 9, 1996 | 120 |
| | | Pertussis risk 1-dose series | | | | |
| Pneumococcal | Not Immune | | | | | |
| | | Pneumococcal 4-dose series | | | | |
| | | Pneumococcal dose 2 at 7 months series | | | | |
| | | Pneumococcal start at 12 months series | 1 | Past Due | May 9, 1997 | 133 |
| | | Pneumococcal start at 24 months series | 1 | Due in Future | May 9, 1998 | 133 |
| | | Pneumococcal risk 2-6 years 2-dose series | | | | |
| | | Pneumococcal risk 1-dose series | | | | |
| | | Pneumococcal risk 2-dose PCV-PPSV series | | | | |
| | | Pneumococcal risk 2-dose PPSV-PCV series | | | | |
| | | Pneumococcal adult risk 2-dose PPSV-PCV series | | | | |
| | | Pneumococcal risk 3-dose series PCV-PPSV-PPSV | | | | |
| | | Pneumococcal risk 6-18 years 3-dose PPSV23-PCV13-PPSV23 series | | | | |
| | | Pneumococcal risk adult 3-dose PPSV23-PCV13-PPSV23 series | | | | |
| | | Pneumococcal risk 6-18 years 3-dose PPSV23-PPSV23-PCV13 series | | | | |
| | | Pneumococcal risk adult 3-dose PPSV23-PPSV23-PCV13 series | | | | |
| | | Pneumococcal 65+ 2-dose PCV13-PPSV23 series | 1 | Due in Future | May 9, 1961 | 133 |
| | | Pneumococcal 65+ 2-dose PPSV23-PCV13 series | 1 | Due in Future | May 9, 1961 | 33 |
| Polio | Not Immune | | | | | |
| | | Polio 4-dose IPV series | 4 | Due in Future | May 9, 2000 | 10, 110, 120, 130 |
| | | | 1 | Valid | Jul. 9, 1996 | 120 |
| | | | 2 | Valid | Sep. 9, 1996 | 120 |
| | | | 3 | Valid | Nov. 9, 1996 | 120 |
| | | Polio 5-dose IPV series | 4 | Recommend | Nov. 9, 1996 | 10, 110, 120, 130 |
| | | | 1 | Valid | Jul. 9, 1996 | 120 |
| | | | 2 | Valid | Sep. 9, 1996 | 120 |
| | | | 3 | Valid | Nov. 9, 1996 | 120 |
| | | Polio 4-dose mixed IPV-OPV series | 4 | Due in Future | May 9, 2000 | 10, 110, 120, 130 |
| | | | 1 | Valid | Jul. 9, 1996 | 120 |
| | | | 2 | Valid | Sep. 9, 1996 | 120 |
| | | | 3 | Valid | Nov. 9, 1996 | 120 |

TABLE 2-continued

Example patient state

| antigen | antigen status | series | dose | dose status | forecast date | preferred CVX |
|---|---|---|---|---|---|---|
| | | Polio 4-dose OPV series | 1 | Past Due | Sep. 5, 1996 | 2 |
| | | Polio risk adult series | | | | |
| | | | 1 | Extraneous | Jul. 9, 1996 | 120 |
| | | | 1 | Extraneous | Sep. 9, 1996 | 120 |
| | | | 1 | Extraneous | Nov. 9, 1996 | 120 |
| Rabies | Not Immune | | | | | |
| | | Rabies risk 3-dose continuous series | | | | |
| | | Rabies risk 3-dose frequent series | | | | |
| Rotavirus | Not Immune | | | | | |
| | | Rotavirus 3-dose series | | | | |
| | | | 1 | Aged Out | Aug. 22, 1996 | |
| | | Rotavirus late start at 15 weeks 3-dose series | | | | |
| | | | 1 | Aged Out | Jan. 10, 1997 | |
| | | Rotavirus 2-dose series | | | | |
| | | | 1 | Aged Out | Aug. 22, 1996 | |
| | | Rotavirus late start at 15 weeks 2-dose series | | | | |
| | | | 1 | Aged Out | Jan. 10, 1997 | |
| Rubella | Not Immune | | | | | |
| | | Rubella 2-dose series | 1 | Recommend | May 9, 1997 | 3, 94 |
| | | Rubella risk 1-dose series | | | | |
| Tetanus | Not Immune | | | | | |
| | | Tetanus standard series | 4 | Eligible | May 5, 1997 | 20, 28, 106, 120 |
| | | | 1 | Valid | Jul. 9, 1996 | 120 |
| | | | 2 | Valid | Sep. 9, 1996 | 120 |
| | | | 3 | Valid | Nov. 9, 1996 | 120 |
| Typhoid | Not Immune | | | | | |
| | | Typhoid risk 1-dose series | | | | |
| | | Typhoid risk 4-dose series | | | | |
| Varicella | Not Immune | | | | | |
| | | Varicella childhood 2-dose series | 1 | Recommend | May 9, 1997 | 21, 94 |
| | | Varicella 13+ 2-dose series | 1 | Due in Future | May 9, 2009 | 21 |
| Yellow Fever | Not Immune | | | | | |
| | | Yellow Fever risk 1-dose series | | | | |
| Zoster | Not Immune | | | | | |
| | | Zoster 2-dose series | 1 | Due in Future | May 9, 1946 | 187 |
| | | Zoster 3-dose series | 1 | Due in Future | May 9, 1956 | 121 |

The method of event-driven health and wellness decision support obviates the need to enumerate patient states by building patient states as events are processed. Each handler processes only a single granular event; it does not attempt to process the whole patient state at once. Handlers can be kept simple and few in number. Even uncommonly occurring patient states are properly handled. The code base is kept small, leading to simplified testing and maintenance.

"Complexity", when applied to computer algorithms, has a formal meaning which is related to the computing resources inherently required by an algorithm to produce a result. Generally speaking, "complexity" classifies algorithms according to the mathematical function by which the computing resources of time and space required grow as a function of the size of the input. If required computing resources are constant regardless of the size of the input, then complexity is constant. If required resources grow linearly with the size of the input, then the algorithm is of linear complexity, called "Order n" ($O(n)$), where n=the size of the input. If required computing resources grow exponentially, as $O(n^k)$, where k is a constant, then the algorithm is of polynomial complexity. An $O(n)$ algorithm is considered superior to an $O(n^k)$ algorithm, because the resources of time and space required by the latter grow very, very quickly as the input grows relative to those required by the former.

Thus, clinical decision support methods that must be capable of computing every possible person state tends toward $O(n^k)$ complexity, because the number of possible person states is exponentially related to the size of the input. The method of event-driven health and wellness decision support by contrast is $O(n)$ as complexity increases only linearly with the size of the input, as the size of the patient state increases linearly with the size of the schedule, and the number of patient states increases linearly with the number of input events.

The complexity factors become more important as new domains such as wellness are tackled. While most individuals visit doctors a handful of times per year, people eat every day and ideally exercise several times a week. The quantity of data managed by wellness apps increases by several orders of magnitude over medical records, leading to a greater number of possible patient states.

An embodiment that also saves the event queue as it is processed provides a way to re-process part of it, for example if a record of a past event is received out of order, improving performance over methods that must re-process all input if any component changes.

Because it processes each event in order, the method of event-driven health and wellness decision support also correctly captures the differences in patient states that may occur when events occur in different orders, as for example when real world events occur in slightly different orders.

Likewise, the method of event-driven health and wellness decision support improves the accuracy and completeness of detail for analysis purposes. As successive patient states are computed as events in the event queue are processed, the schedule or schedules in effect at each value of Now may be used. For example, different vaccine schedules in effect at different times may evaluate an immunization history differently, and produce different recommendations, which may affect the evaluation of provider performance or vaccine coverage rates for a population, making it important to use the schedule that was in effect at the time. An embodiment that saves each patient state at continuous effective date/time ranges provides a complete and accurate database across both the dimensions of time and patient state detail.

The analytics in turn provide feedback on the effectiveness of best practices and allows the best practices to be adjusted over time. Clinical trials tend to isolate one variable at a time. By contrast, the method of event-driven health and wellness decision support, due to its complexity characteristics, allows the interactions among an empirical or simulated set of factors to be studied. One can expect such analytics to give rise to improved best practices, enabling the method of event-driven health and wellness decision support to more effectively drive behavior toward the goal of optimal health and wellness.

As an example, the dates at which individuals in a population actually receive vaccines relative to the dates at which they are eligible to receive them could be correlated with the dates of various public policy initiatives, such as the start of school, the implementation of an immunization registry, and so forth.

As another example, the administration of vaccines to a population according to an immunization schedule, as indicated by the past events of individuals in a population, could be analyzed against both disease outbreak and vaccine adverse event occurrences, possibly resulting in best practices adjustments which more effectively balance immunization benefits and harms.

It is to be understood that the method of event-driven health and wellness decision support is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

What is claimed is:

1. A method for performing event-driven health and wellness decision support, comprising the steps of:
creating an initial person state comprising a composite set of initial data elements;
setting a previous person state to the initial person state;
receiving a schedule, said schedule comprising at least one composite set of schedule data elements, the at least one composite set of schedule data elements comprising parameters that specify conditions under which particular updates of a particular subset of person state data elements of a person state are to be performed;
some schedules describing one or more series of events and specifying particular values to be assigned to a particular subset of event data elements of each subsequent event in each of the one or more series of events based upon parameters specifying values of a particular subset of event data elements of a previous event in the one or more series of events;
receiving at least one health-and-wellness record, wherein the at least one health-and-wellness data elements comprises a composite set of health-and-wellness data elements, one or more health-and-wellness data elements in the composite set of health-and-wellness data elements representing real world events, each data element in the composite set of health-and-wellness data elements that represents a real world event having a timestamp, wherein the at least one health-and-wellness record is associated with an individual person, the at least one health-and-wellness record having a timestamp;
creating at least one event upon receiving the at least one health-and-wellness record, wherein the at least one event comprises a set of event data elements;
initializing a subset of the event data elements of the at least one event from a subset of the health-and-wellness data elements of the at least one health-and-wellness record;
assigning to the at least one event the timestamp of one of the data elements in the composite set of health-and-wellness data elements representing a real world event;
associating the at least one event with the individual person associated with the at least one health-and-wellness record;
associating the at least one event with at least one handler, wherein the at least one handler comprises a software module executing on a computer;
inserting the at least one event into an event-queue in timestamp order;
processing the at least one event in the event-queue in the timestamp order by executing the at least one handler, wherein the at least one handler creates a new person state by replicating the previous person state;
assigning to the new person state the timestamp of the at least one event;
associating the new person state with the individual person associated with the at least one event;
comparing a combination of a subset of new person state data elements in the new person state and a subset of event data elements in the at least one event to the parameters in the schedule that specify the conditions under which the particular updates of the particular subset of person state data elements of the person state are to be performed;
performing the particular updates to the particular subset of person state data elements in the new person state when the combination of the subset of person state data elements in the new person state and the subset of data elements in the at least one event match said parameters; and
resetting the previous person state as the new person state;
comparing a particular subset of the event data elements of the event associated with the handler to the parameters of the schedule specifying values of a particular subset of event data elements of a previous event in the one or more series of events; and
performing the following set of steps when the particular subset of the event data elements of the event associated with the handler matches the parameters of the schedule specifying values of a particular subset of event data elements of a previous event in the one or more series of events:
creating one or more additional events;
associating each said additional event in the one or more additional events with the individual person associated with the event associated with the handler;
assigning an additional timestamp to the additional event in the one or more additional events; and
assigning particular values to a particular subset of additional event data elements of each said additional event in the one or more additional events according to the schedule, wherein each event is associated with an event-type, wherein the person states comprise a data set subject to combinatorial explosion when operated upon by processing events, and wherein person states are updated on-demand to a predetermined target and each handler of the at least one handler processes only a singular event-type, thereby avoiding the combinatorial explosion.

2. The method for performing event-driven health and wellness decision support of claim 1, wherein the at least one health-and-wellness record is received in the timestamp order.

3. The method for performing event-driven health and wellness decision support of claim 1, wherein the at least one health-and-wellness record is received out of the timestamp order.

4. The method for performing event-driven health and wellness decision support of claim 1, wherein the method is replicated to apply to a population.

5. The method for performing event-driven health and wellness decision support of claim 1, wherein the at least one event is processed in the event-queue in the timestamp order until the person state matches specified criteria.

6. The method for performing event-driven health and wellness decision support of claim 1, wherein the at least one event is processed in the event-queue in the timestamp order until a last one of the events in the event queue has been processed.

7. The method for performing event-driven health and wellness decision support of claim 1, wherein the at least one health-and-wellness record represents one or more simulated events in a plurality of simulated events.

8. The method for performing event-driven health and wellness decision support of claim 1, wherein the processing of the at least one event in the event-queue in the timestamp order is paused and resumed.

9. The method for performing event-driven health and wellness decision support of claim 1, wherein each said previous person state is saved in a computer-readable medium.

* * * * *